United States Patent
Knutsson et al.

(10) Patent No.: US 9,642,989 B2
(45) Date of Patent: *May 9, 2017

(54) CATHETER NEEDLE TIP SHIELDING DEVICE

(71) Applicant: VIGMED AB, Helsingborg (SE)

(72) Inventors: Per Knutsson, Helsingborg (SE); Robert Domonkos, Lomma (SE)

(73) Assignee: Vigmed AB, Helsingborg (SE)

( * ) Notice: Subject to any disclaimer, the term of this patent is extended or adjusted under 35 U.S.C. 154(b) by 187 days.

This patent is subject to a terminal disclaimer.

(21) Appl. No.: 14/076,374

(22) Filed: Nov. 11, 2013

(65) Prior Publication Data
US 2014/0121604 A1    May 1, 2014

Related U.S. Application Data

(63) Continuation of application No. 13/388,985, filed as application No. PCT/SE2010/050884 on Aug. 13, 2010, now Pat. No. 8,632,500.
(Continued)

(30) Foreign Application Priority Data

Aug. 13, 2009    (SE) .................... 0950587-6

(51) Int. Cl.
A61M 25/06    (2006.01)
A61M 5/32    (2006.01)

(52) U.S. Cl.
CPC ....... *A61M 25/0618* (2013.01); *A61M 5/3273* (2013.01)

(58) Field of Classification Search
CPC .......... A61M 25/0618; A61M 25/0625; A61M 5/3273; A61M 5/3216; A61M 2005/325;
(Continued)

(56) References Cited

U.S. PATENT DOCUMENTS 3,469,579 A    9/1969    Hubert
3,589,361 A    6/1971    Loper et al.
(Continued)

FOREIGN PATENT DOCUMENTS

CN    1547493 A    11/2004
CN    101500637 A    8/2009
(Continued)

OTHER PUBLICATIONS

International Search Report dated Dec. 8, 2010 issued in International Application No. PCT/SE2011/050884.
(Continued)

*Primary Examiner* — Nathan R Price
*Assistant Examiner* — Melissa A Snyder
(74) *Attorney, Agent, or Firm* — Fishman Stewart PLLC (57) ABSTRACT

The present invention discloses a catheter instrument 1000 comprising a needle tip shielding device 100, a catheter hub 200 and a needle unit 300, wherein the needle unit 300 is provided with connecting means 301 for connection to the catheter hub 200, and with connecting means 302 for connection to an external device. The needle tip shielding device 100 is comprising a body with a rear side 106, a front side 107, an outer surface 108 connecting the rear side 106 and the front side 107, a hole 102 extending from the rear side 106 to the front side 107, and a resilient arm 103 extending at an attachment point 105 from the front side 107 of the body; wherein the resilient arm 103 has a resting stale from which it may be forced to yield free passage through the hole 102 in an axial direction of the body, the resilient arm 103 being adapted for clamping a needle tip 304 of a hollow needle 303 extending through the hole 102 in a direction from the rear side 106 to the front side 107, when being in the resting state.

20 Claims, 4 Drawing Sheets

Related U.S. Application Data (60) Provisional application No. 61/235,438, filed on Aug. 20, 2009.

(58) Field of Classification Search
CPC .............. A61M 5/3275; A61M 5/3219; A61B 17/3494
See application file for complete search history.

(56) References Cited

U.S. PATENT DOCUMENTS

| | | | |
|---|---|---|---|
| 4,820,277 A | 4/1989 | Norelli | |
| 4,929,241 A | 5/1990 | Kulli | |
| 4,982,842 A | 1/1991 | Hollister | |
| 5,053,017 A | 10/1991 | Chamuel | |
| 5,132,369 A | 7/1992 | Yasuda et al. | |
| 5,135,504 A | 8/1992 | McLees | |
| 5,151,089 A | 9/1992 | Kirk et al. | |
| 5,188,611 A | 2/1993 | Orgain | |
| 5,242,417 A | 9/1993 | Paulder | |
| 5,312,369 A | 5/1994 | Arcusin | |
| 5,344,408 A | 9/1994 | Partika | |
| 5,458,658 A | 10/1995 | Sircom | |
| 5,490,841 A | 2/1996 | Landis | |
| 5,558,651 A | 9/1996 | Crawford et al. | |
| 5,599,313 A | 2/1997 | Gyure et al. | |
| 5,603,699 A | 2/1997 | Shine | |
| 5,885,249 A | 3/1999 | Irisawa | |
| 6,197,001 B1 | 3/2001 | Wilson | |
| 6,413,243 B1 | 7/2002 | Geist | |
| 6,616,630 B1 | 9/2003 | Woehr et al. | |
| 7,347,838 B2 * | 3/2008 | Kulli .............. | A61M 5/3273 604/164.08 |
| 7,530,965 B2 * | 5/2009 | Villa .................. | A61M 5/3273 604/110 |
| 7,704,239 B2 | 4/2010 | Raulerson et al. | |
| 7,935,080 B2 | 5/2011 | Howell et al. | |
| 8,038,654 B2 | 10/2011 | Lim et al. | |
| 8,337,471 B2 | 12/2012 | Baid | |
| 8,403,886 B2 | 3/2013 | Bialecki et al. | |
| 8,414,539 B1 | 4/2013 | Kuracina et al. | |
| 8,496,623 B2 | 7/2013 | Burkholz | |
| 8,632,500 B2 | 1/2014 | Knutsson et al. | |
| 2002/0099342 A1 | 7/2002 | Zurcher | |
| 2002/0193744 A1 | 12/2002 | Alesi et al. | |
| 2003/0105431 A1 * | 6/2003 | Howell ............... | A61M 5/3273 604/164.08 |
| 2004/0049155 A1 | 3/2004 | Schramm | |
| 2004/0225260 A1 | 11/2004 | Villa et al. | |
| 2000/5277879 | 12/2005 | Daga | |
| 2005/0277879 A1 | 12/2005 | Daga | |
| 2006/0270979 A1 | 11/2006 | Simas et al. | |
| 2007/0038179 A1 * | 2/2007 | Bialecki ............. | A61M 5/3273 604/110 |
| 2007/0100296 A1 | 5/2007 | Hwang | |
| 2008/0097344 A1 | 4/2008 | McKinnon et al. | |
| 2008/0208138 A1 | 8/2008 | Lim et al. | |
| 2008/0249478 A1 * | 10/2008 | Ishikura ............ | A61M 25/0618 604/198 |
| 2008/0269693 A1 | 10/2008 | Steube et al. | |
| 2009/0088696 A1 | 4/2009 | Harding et al. | |
| 2009/0163861 A1 | 6/2009 | Carlyon | |
| 2012/0130321 A1 | 5/2012 | Woehr | |
| 2012/0136311 A1 | 5/2012 | Knutsson | |
| 2012/0296282 A1 | 11/2012 | Koehler et al. | |
| 2013/0030371 A1 | 1/2013 | Knutsson | |
| 2013/0178800 A1 | 7/2013 | Domonkos et al. | |
| 2014/0135713 A1 | 5/2014 | Domonkos | |

FOREIGN PATENT DOCUMENTS

| | | |
|---|---|---|
| CN | 102470236 A | 8/2009 |
| CN | 101687083 A | 3/2010 |
| CN | 202875975 | 4/2013 |
| DE | 10 2008 002 796 A1 | 9/2009 |
| EP | 0 489 419 A1 | 6/1992 |
| EP | 0 657 184 | 6/1995 |
| EP | 0 887 082 A2 | 12/1998 |
| EP | 2 016 963 A1 | 1/2009 |
| EP | 2 204 204 A1 | 7/2010 |
| GB | 2 451 153 A | 9/2009 |
| JP | H06-315532 A | 11/1994 |
| JP | H08-276013 A | 10/1996 |
| JP | 2001-112872 | 4/2001 |
| JP | 2001-514943 A | 9/2001 |
| JP | 2002085558 A | 3/2002 |
| JP | 2005-529717 A | 10/2005 |
| JP | 2008-522739 A | 7/2008 |
| JP | 2010-500150 A | 1/2010 |
| SE | 1150633 A1 | 1/2013 |
| WO | WO 91/01151 A1 | 2/1991 |
| WO | WO 01/68174 A2 | 9/2001 |
| WO | WO 2005/042080 A1 | 5/2005 |
| WO | WO 2005/079891 A1 | 9/2005 |
| WO | WO 2006/079766 A1 | 8/2006 |
| WO | WO 2008/021132 A1 | 2/2008 |
| WO | WO 2008/076459 A1 | 6/2008 |
| WO | WO 2009/010847 A2 | 1/2009 |
| WO | WO 2009/123025 A1 | 10/2009 |
| WO | WO 2011/019316 A1 | 2/2011 |
| WO | WO 2013/006134 A1 | 1/2013 |

OTHER PUBLICATIONS

International Search Report dated Jul. 11, 2011 issued in International Application No. PCT/SE2011/050443.

International Search Report dated Dec. 21, 2011 issued in International Application No. PCT/SE2011/051140.

Notification of Transmittal of International Preliminary Report on Patentability mailed Jul. 17, 2012.

Chinese Office Action (with translation) dated Jul. 4, 2014 issued in Chinese Application No. 2011800189380.

International Search Report dated Sep. 27, 2012 issued in International Application No. PCT/SE2012/050771.

Japanese Office Action (with translation) dated Dec. 16, 2014 issued in Japanese Application No. 2013-504851.

* cited by examiner

CATHETER NEEDLE TIP SHIELDING DEVICE

This is a continuation of U.S. application Ser. No. 13/388,985, filed Feb. 4, 2012, which is a National Phase Application under 35 U.S.C. 371 of PCT/SE2010/050884 filed Aug. 13, 2010, and claims priority under 35 USC 365(a)-(c) to Swedish Application No. 0950587-6 filed Aug. 13, 2009, and to U.S. Provisional Application 61/235,438 filed Aug. 20, 2009, the contents of which are incorporated herein by reference.

TECHNICAL FIELD

The present invention relates to a catheter instrument comprising a needle tip shielding device for the automatic safety shielding of a needle after its employment for introduction of a catheter tube.

BACKGROUND

The clinical utilization of a pointed hollow needle mounted inside a flexible catheter tube is well known in the medical art for the introduction of a catheter. In such a medical instrument, the catheter tube is positioned tightly around the needle in such a way as to allow the needle to slide and telescope along the length of the catheter tube. Before use, the tip of the needle is protruding slightly through the opening of the catheter tube to allow facile penetration through the skin. Upon puncturing of the skin and introduction of the needle, the distal end of the catheter tube is simultaneously brought into place inside the desired target body cavity of the patient, such as the inside of a blood vessel, for example a vein. The needle has then done its duty in assisting the introduction of the catheter and is withdrawn by being pulled backwards through the catheter. Upon release of the needle, the catheter is set in its intended working mode extending over a lengthier period of time and including, for example, periodical administration or infusion of fluids or medications in liquid form, the collection of blood samples and the like.

An unprotected released needle constitutes, however, a serious health hazard due to the fact that it may be contaminated with e.g. infectious agents originating from the patient's blood or other body fluids, in combination with the needle tip's inherent ability to easily penetrate skin. Hence, the medical personnel who are handling the released needle may acquire the corresponding disease, e.g. HIV or hepatitis, if by accident contacting it with their skin. In order to circumvent or alleviate the health hazards associated with such a released needle amongst other things, there has been much effort devoted to the development of various kinds of needle tip protectors with a special focus on automatic variants of a type which may be referred to as being "foolproof".

U.S. Pat. No. 6,616,630 B1, by B. Braun Melsungen A. G. discloses a safety IV catheter comprising a resilient spring clip normally positioned in the catheter hub. The needle of the safety IV catheter passes through a hole in the spring clip which allows axial movement of the needle. When the needle is in the forward position, i.e. when the safety IV catheter is ready for use, the presence of the needle forces parts of the spring clip into a position where these parts locks to the inside of the catheter hub, whereby movement of the spring clip relative the catheter hub is prevented. As the needle is withdrawn to a point where the tip passes these parts, the spring clip snaps into a position in which it is blocking access to the to the tip of the needle. Simultaneously, the part of the spring clip that previously locked to the inside of the catheter hub snap out of this position, whereby movement of the spring clip relative the catheter hub may occur. As the needle is further withdrawn, means are provided, e.g. a slot or a crimp on the needle, to lock the spring clip to the needle, whereby the spring clip is ejected from the catheter hub together with, and positioned on, the needle.

For various reasons, including e.g. practical, economical and technical reasons, the above described spring clips, and similar marketed variants, are today by necessity made of metal and catheter hubs of a plastic material. Disadvantages of the combination of these materials in this application include the release of e.g. microscopic plastic chips and metallic particles by the scraping of the metal spring clip against the inside of the plastic catheter hub when the former is ejected from the latter upon withdrawal of the needle. These chips and particles may easily be flushed into the bloodstream of a patient upon normal use of the corresponding catheter, and thus represent a serious health hazard to the same.

Spring clips, like the type described above and similar marketed variants, and needles, are today both by necessity made of metal. One disadvantage of the spring clip of this and similar safety IV catheters is the scraping vibration generated as the needle slides through and on the spring clip as it is withdrawn. This scraping vibration, which is due to metal sliding over metal and which can be clearly heard and felt, is highly uncomfortable and worrisome to the patient, who already is in an uncomfortable and exposed situation and may be very anxious.

Furthermore, spring clips, like the type disclosed above, provide poor protection per se against drops of blood or body fluid that may move outwards from the interior of the catheter hub as the needle is removed. Such drops may, for example, spread infectious diseases.

GB2451153(A) by Poly Medicure Ltd discloses a needle safety device for an intravenous catheter apparatus that includes a base capable of receiving a needle between opposing jaws attached to the base and capable of being influenced by the needle. The jaws have a link connecting the jaws arranged a distance from the base. The jaws may move between an expanded position in which they interact with an obstruction within a wing housing of the intravenous catheter apparatus. The jaws permit relative movement of the needle with the base when expanded, close around a needle tip as it passes the jaws, and prevent relative movement of the needle with the base when the jaws are collapsed.

However, when collapsed, each and one of the jaws do not extend further than maximally to the center axis of the needle. The particular jaw, onto which the tip of the needle is pointing, may thus relatively easy reveal the needle tip if it happens to be bent. In addition, the jaws need to be forced together with a link. This link represents an additional part of the device, which increases cost and complicates production of the same.

EP657184(A1) by the BOC Group plc discloses a medical device, for example, an IV cannula or a syringe which has a hollow needle with a sharp distal end for piercing the skin of a patient and includes means for protecting the sharp end of the needle after use to minimize the possibility of accidental needle stick. The means includes a rod mounted for movement through the needle between a needle end protection position and a retracted position within the hollow needle, and means for maintaining the rod towards the needle end protection position.

However, since the needle tip is not protected in the protection position there is a risk that the needle may cause dermal wounds if the needle engages the skin close to parallel or at a minor angle towards the skin.

Hence, an improved device for automatic shielding of the needle tip of a needle after its employment for introduction of a catheter tube is desired.

SUMMARY

It is an object of the present invention, considering the disadvantages mentioned above, to provide a safety catheter instrument and needle tip shielding device which is devoid of scraping vibrations, or where these vibrations are reduced, as the needle is withdrawn.

It is another object of the present invention to provide a needle tip shielding device with an improved protection per se against drops of blood or body fluid that may move outwards from the interior of the catheter hub as tire needle is withdrawn from a safety catheter instrument.

It is yet another object of the present invention to provide a needle tip shielding device which may be withdrawn from a catheter hub with a minimized risk for the generation of internal scratches on the interior surface of the latter.

It is yet another object of the present invention to provide a needle tip shielding device which may be withdrawn from a catheter hub with a minimized risk for the generation of loose particles, such as particles of plastic or metal.

It is yet another object of the present invention to provide a needle tip shielding device with improved safety with regard to the shielding of the needle tip.

It is yet another object of the present invention to provide a needle tip shielding device which may be easily manufactured at a low cost.

These and other objects, which will appear from the following description, have now been achieved by a device according to one aspect of the present invention which comprises a plastic needle tip shielding device comprising a body with a rear side; a front side, an outer surface connecting the rear side and the front side, a hole extending from the rear side to the front side, and a resilient arm extending at an attachment point from the front side of the body; wherein the resilient arm has a resting state from which it may be forced to yield free passage through the hole in an axial direction of the body, the resilient arm being adapted for clamping a needle tip of a hollow needle extending through the hole in a direction from the rear side to the front side, when being in the resting state; and wherein any straight imaginary line extending longitudinally through the hole in the axial direction of the body coincides with a point on the surface of the resilient arm, or an elongation thereof, when the resilient arm is in the resting state.

According to another aspect of the present invention, the needle tip shielding device may be shaped as a circular or distorted cut cone or cylinder.

According to yet another aspect of the present invention, the needle tip shielding device may be provided with a back-hooking elongation, the resilient arm together with the back hooking elongation thereof may have an L-shaped form; wherein the any straight imaginary line coincides with a point on the surface of the resilient arm in between the attachment point and an inner corner in the L-shaped form of the resilient arm, when the resilient arm is in the resting state; and wherein the any straight imaginary line coincides with a point on the surface of the back-hooking elongation, or with a point on the surface in between the attachment point and the corner, when the resilient arm is clamping the needle tip in cooperation with the back-hooking elongation.

According to yet another aspect of the present invention, the resilient arm of the needle tip shielding device, or any elongation thereof, may have a maximum of one external point of contact, the point of contact being a contact with any part of the hollow needle, when used.

According to yet another aspect of the present invention, the inner diameter of the hole may be equal to or slightly larger than the outer diameter of the shaft of the hollow needle to provide a sliding and directing engagement between the shaft and the needle tip shielding device.

According to another aspect of the present invention, the needle tip shielding device may comprise a body shaped as a circular or distorted cut cone or cylinder with a rear side, a front side, an outer surface connecting the rear side and the front side, a hole extending from the rear side to the front side, and a resilient arm extending at an attachment point from the front side of the body; wherein the resilient arm has a resting state from which it may be forced to yield free passage through the hole in an axial direction of the body, the resilient arm together with a back-hooking elongation thereof having an L-shaped form for clamping a needle tip of a hollow needle extending through the hole in a direction from the rear side to the front side; wherein any straight imaginary line extending longitudinally through the hole in the axial direction of the body coincides with a point on the surface of the resilient arm in between the attachment point and an inner corner in the L-shaped form of the resilient arm, when the resilient arm is in the resting state; wherein any of the before mentioned straight imaginary lines coincides with a point on the surface of the back-hooking elongation, or with a point on the surface in between the attachment point and the corner, when the resilient arm is clamping and thus protecting the needle tip in cooperation with the back-hooking elongation; and wherein the resilient arm or the back-hooking elongation has a maximum of one external point of contact, the point of contact being a contact with any part of the hollow needle, when used.

According to another aspect of the present invention, the needle tip shielding device may be made of a molded plastic material. In this respect, the needle tip shielding device may be molded, such as for example injection molded, into one homogenous piece and/or one integral unit, without interfaces in between the different parts thereof.

According to yet another aspect, the outer surface may be provided with at least one protuberance.

According to yet another aspect, the rear side may be provided with a cone-shaped elevation through which the hole is extending.

According to yet another aspect, the rear side may be larger than the front side to form an inclination of the outer surface within the range from 0° to 10°.

According to yet another aspect, the length of the back-hooking elongation, measured from the corner to the most protruding part, may be 0.5 to 6 times the diameter of the hole.

According to yet another aspect, the angle inside the corner may be within the range from 60° to 110°.

According to yet another aspect, the body may be elliptic.

According to yet another aspect, the resilient arm of the needle tip shielding device may be provided with a back-dragging preventing elongation for prevention of unintentional movement of the needle tip shielding device in the direction from the front side to the rear side, when the needle tip shielding device is mounted in a catheter instrument.

According to yet another aspect, the front side of the needle tip shielding device may be provided with a longitudinal arm for additional protective shielding of the needle tip or the hollow needle.

According to yet another aspect of the present invention, there is provided a catheter instrument comprising the needle tip shielding device, a catheter hub and a needle unit; wherein the needle unit is provided with connecting means for connection to the catheter hub, with connecting means for connection to an external device, and is fixed around the rear end of the hollow needle; and wherein the catheter hub is connected to a catheter extending longitudinally in the same direction as the hollow needle when the needle unit is connected by the connecting means to the catheter hub.

Further features of the invention and its embodiments are set forth in the appended claims.

BRIEF DESCRIPTION OF THE DRAWINGS

These and other aspects, features and advantages of which the invention is capable will be apparent and elucidated from the following description of non-limiting embodiments of the present invention, reference being made to the accompanying drawings, in which.

DETAILED DESCRIPTION OF THE EMBODIMENTS

Embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

Embodiments of the present invention will now be described below with reference to FIGS. 1 to 7.

Figure 1:
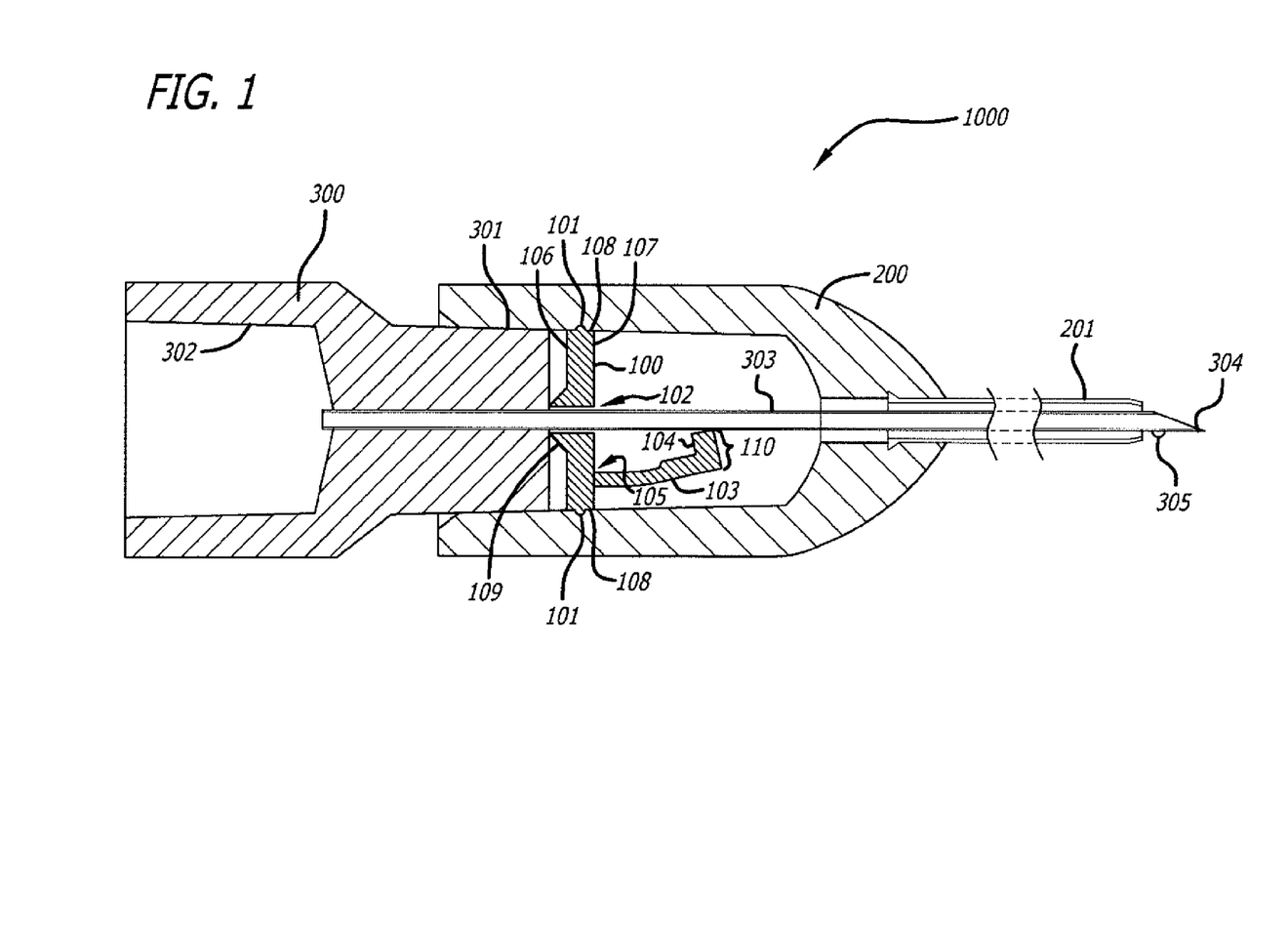
FIG. 1 is a cross section view from the side of a catheter instrument according to one embodiment in the ready mode, i.e. before its use for the introduction of a catheter tube, comprising a needle tip shielding device according to one embodiment, a catheter hub and a needle unit, according to an embodiment of the present invention.

Referring to FIG. 1, there is provided a catheter ins run ent 1000 comprising a needle tip shielding device 100, a catheter hub 200 and a needle unit 300. The needle unit 300 is provided with connecting means 301 for connection to the catheter hub 200, and with connecting means 302 for connection to an external device, for example a syringe or the like. It is mechanically and hermetically fixed as known in the art, such as molded or glued, around the rear end of a hollow needle 303, whereby liquid passage is allowed in both directions, from the rear end of the needle unit 300 to and through a needle tip 304 of the hollow needle 303. The hollow needle 303 may be made of metal and of a type commonly used and well known in the medical art to penetrate the skin of a patient.

The needle tip shielding device 100 is fitted inside the catheter hub 200 so that the outer surface of the former is contacting the inner surface of the latter, via a catheter hub contact area. Movement of the needle tip shielding device 100, relative the catheter hub 200, may be restricted by means of at least one protuberance 101, comprising the catheter hub contact area, located on the outer surface 108 of the needle tip shielding device 100. Protuberance 101 is making a corresponding imprint in, and where it contacts, the inner surface of the catheter huh 200. The hollow needle 303 is longitudinally movable through a hole 102 in the needle tip shielding device 100. The hole 102 has a diameter adapted for the hollow needle 303 to be able to slide therein. The diameter of the hole 102 may, for example, be slightly larger that the outer diameter of the hollow needle 303, or the same. The hollow needle 303 is provided with an expansion region 305 near the needle tip 304. The expansion region 305 is a region on the hollow needle 303 where the effective diameter is larger than elsewhere on the needle in the direction towards the rear hollow needle 303. An increase in the effective diameter of the hollow needle 303 by expansion region 305 has the effect that this region is not movable through the hole 102.

The needle tip shielding device 100 is provided with a resilient arm 103, which is held out of its three dimensional equilibrium state, i.e. its normal resting position or resting state, by the outer surface of the hollow needle 303. The hollow needle 303 is, despite its contact with the resilient arm 103, longitudinally movable as it is arranged to slide on the same. The catheter hub 200 is connected to a catheter 201, which extends longitudinally in the same direction as the hollow needle 303. The catheter 201 is preferable flexible and of a type commonly used and well known in the medical art. The inner diameter of the catheter 201 may be slightly larger than the outer diameter of the hollow needle 303 and arranged so that the latter, as well as expansion region 305, may slide inside the former.

In the ready mode, i.e. before its use for the introduction of a catheter tube, the following characteristics of catheter instrument 1000 are valid: (i) Needle unit 300 is connected by connecting means 301 to the catheter hub 200. (ii) The hollow needle 303 is extending through the hole 102 of the needle tip shielding device 100, which is fitted inside the catheter flub 200, whereby movement of the needle tip shielding device 100 relative the catheter hub 200 is restricted. The hollow needle 303 is contacting the resilient arm 103 whereby this is forced out of its normal resting position. (iii) The hollow needle 303 is further extending through catheter 201 so that the needle tip 304 is protruding slightly past the opening of the catheter 201 in order to facilitate penetration of the skin of a patient.

When in ready mode, the catheter instrument 1000 may be used by a user, such as a nurse or other medical personnel, for the introduction of a catheter tube, such as catheter 201, in accordance with the following sequential steps: (i) Penetration of the skin of a patient by means of needle tip 304, followed by insertion of the catheter 201 so that its opening is located in the desired body cavity, such as the inside of a vein. (ii) Fastening of the catheter hub 200 on the skin of the patient by means well known in the art, such as with medical tape or the like. (iii) Disconnection of connecting means 301, followed by withdrawal of the hollow needle 303 by holding onto and pulling the needle unit 300 backwards until the needle tip shielding device 100 is disconnected, whereby the resilient arm 103 of the needle tip shielding device 100 is protecting the needle tip 304 so that it cannot penetrate skin by accident.

Figure 2:
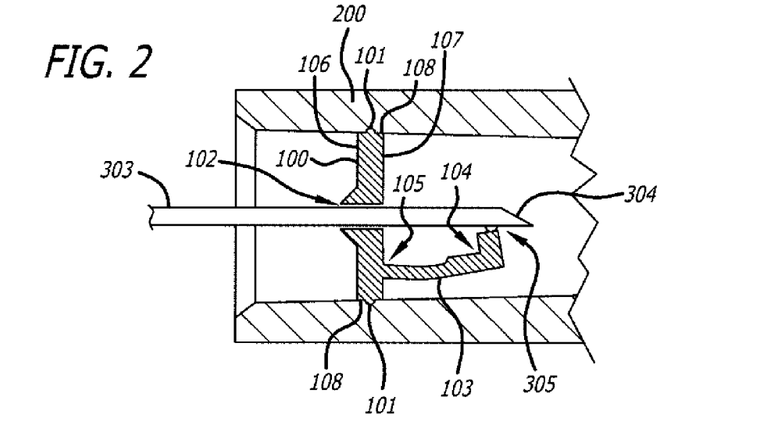
FIG. 2 is a cross section view from the side of a needle tip shielding device according to one embodiment fitted inside a catheter hub with a hollow needle withdrawn to the point where an expansion region reaches a contact point of a resilient arm, according to an embodiment of the present invention.
Figure 3:
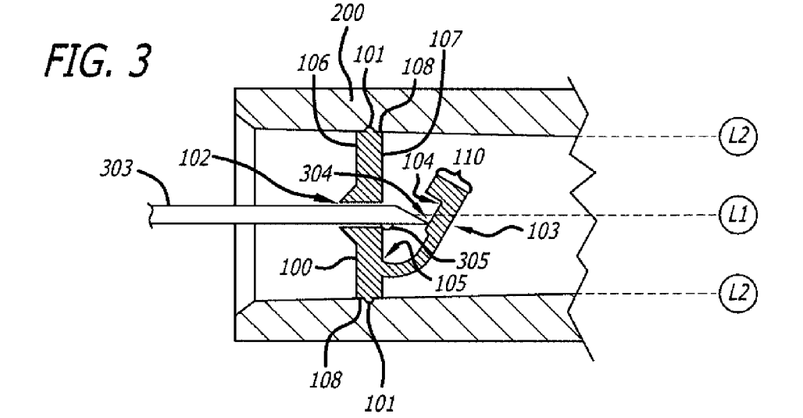
FIG. 3 is a cross section view from the side of a needle tip shielding device according to one embodiment fitted inside a catheter hub with a hollow needle withdrawn to the point where an expansion region reaches a hole, whereby further backwards movement of the hollow needle relative the catheter hub is prevented without disconnection of the needle tip shielding device from the catheter hub, according to an embodiment of the present invention.
Figure 4:
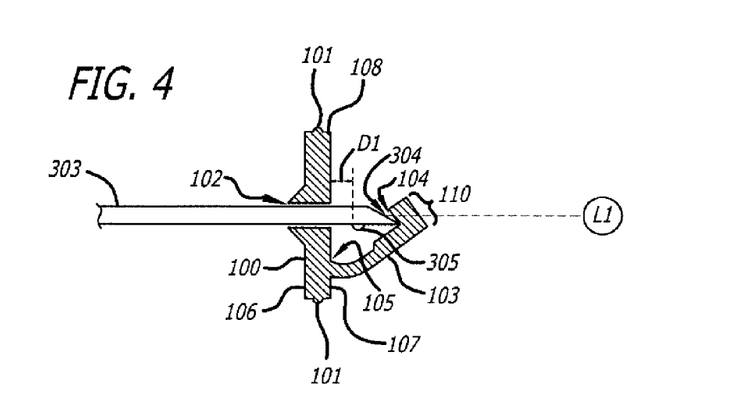
FIG. 4 is a cross section view from the side of a needle tip shielding device according to one embodiment disconnected from the catheter hub, with a hollow needle pushed forward with the rear end of an expansion region a distance D1 from the most forward edge of a hole, whereby a needle tip coincidences with a corner, according to an embodiment of the present invention.

With reference to FIGS. 2, 3 and 4, below follows a detailed description of the various events that occur upon withdrawal of the hollow needle 303 according to (iii) above:

When the hollow needle 303 has been withdrawn to the point where expansion region 305 reaches the contact point of the resilient arm 103, the latter may bend away slightly to allow easy passage of the former upon a slight increase in the force of withdrawal (FIG. 2). If the expansion region 305 is of a particular type and located on the hollow needle 303 such that the resilient arm does not come in contact with any area with increased effective diameter, the resilient arm does not have to bend away slightly. Examples of such an expansion region 305 include a protruding bump, e.g. a butt weld, which is facing away from the contact point of the resilient arm 103 on the hollow needle 303. Examples of other possible expansion regions 305 include a crimp or any other protruding distortion as well known in the art.

Further withdrawal of the hollow needle 303, to the point where the needle tip 304 passes the contact point of the resilient arm 103, results in that the latter strives toward its normal resting position, which is such that a part of the resilient arm 103, or an extension thereof, is in front of the needle tip 304 (FIG. 3). The resting position of the resilient arm 103 is such that the needle tip 304 will always project, in the longitudinal direction of the hollow needle 303, onto a point of the surface of the resilient area 103 which is positioned between a corner 104 and the attachment point 105 of the resilient arm 103 independent of the degree of rotation of the hollow needle 303 around its longitudinal axis. The needle tip 103 is thus clamped and protected by the resilient arm 103.

When drawn backwards beyond this point, the hollow needle 303 may not be pushed in the forward direction again without being hindered by the resilient arm 103, or an extension thereof. Hence, if a user tries to push the hollow needle 303 forwards, the needle tip 304 may penetrate slightly into the resilient arm 103. Preferably the resilient arm 103 is arranged so that this penetration occurs in the corner 104 (FIG. 4).

Even further withdrawal of the hollow needle 303, to the point where the expansion region 305 reaches the hole 102, results in that the hollow needle 303 engages with, i.e. gets stuck in, in the needle tip shielding device 100 (FIG. 3). Additional increase in the force of withdrawal of the hollow needle 303 results in that the needle tip shielding device 100 disconnects from the catheter hub 200. The hollow needle 303 is thereby released from the catheter hub 200 together with the needle tip shielding device 100, which is effectively clamping the needle tip 304 and protecting a user from accidental contact with the same. The force needed to disconnect the needle tip shielding device 100 from the catheter huh 200 is, amongst other factors, depending on the angle between an imaginary line L1, which is equivalent with the extension of the hollow needle 303 and the center of the hole 102, and an imaginary line L2, which is a straight line extending in the same plane as L1 that coincides with two points on the surface of the needle tip shielding device 100 being in contact with the inner surface of the catheter hub 200, the points being located outside the surface of the protuberance 101 (FIG. 3). Preferably this angle is such that the needle tip shielding device 100 is not disconnected from the catheter hub when the hollow needle 303 is withdrawn until the expansion region 305 reaches the hole 102. The needle tip shielding device 100 is, however, preferably easily disconnected when the expansion region 305 reaches the hole 102, such as with, for example, a gentle jerk backwards. When the hollow needle 303 and the needle tip shielding device 100 have been released from the catheter hub 200, or when the needle tip shielding device 100 is fitted inside the catheter hub 200 and the needle tip 304 is clamped by the resilient arm 103, or an extension thereof, the hollow needle 303 might be pushed forward so that the rear end of the expansion region 305 is moved forward a distance D1 from the most forward edge of the hole 102, during which the needle tip 304 may slide on the surface of the resilient arm 103 until it coincides with the corner 104 (FIG. 4).

The Catheter Instrument 1000

Connecting means 301 and 302 may independently be selected from various connection types allowing a user to connect and disconnect the needle unit 300 from the catheter hub 200, and the needle unit 300 from the external device, respectively, as desired. Examples of such connection types include Luer-Lok®, Luer-Slip®, and various types of bayonet sockets or the like, as well known in the art. Preferably, connecting means 301 and 302, in particular connecting means 302, are air tight so that no gas or liquid, such as blood or any other body liquid, may pass.

With reference to FIG. 4, according to one embodiment, the location of the expansion region 305 on the hollow needle 303 is selected such that the distance D1 is minimized while still allowing the resilient arm 103, or an extension thereof, to clamp the needle tip 304 when the hollow needle 303 is withdrawn.

According to one embodiment, the catheter hub 200 may be provided with additional devices and the like to facilitate its placement and optimize its use, as well known in the art. For example, it may be provided with valves, gaskets, fastening devices, means for drying blood residues of the needle, and the like.

The Needle Tip Shielding Device 100

Figure 5:
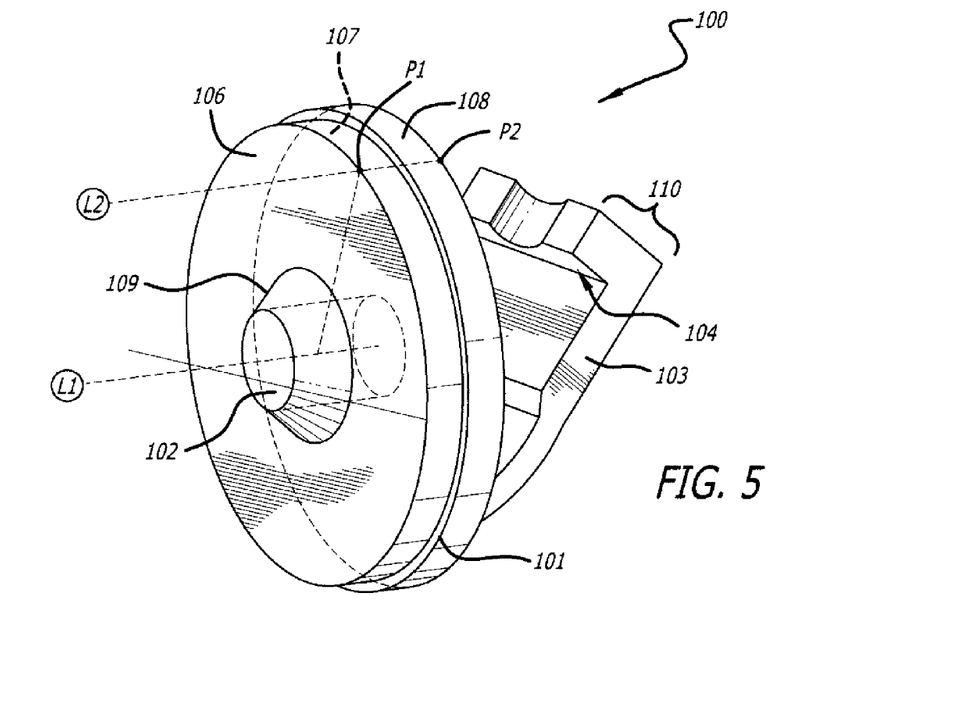
FIG. 5 is a perspective view of a needle tip shielding device according to one embodiment comprising a body with a circular rear side, a circular front side, an outer surface connecting the circular rear side and the circular front side, the circular hole extending from the circular rear side to the circular front side, and a resilient arm extending from the front side of the body, according to an embodiment of the present invention.

With reference to FIG. 5, according to one embodiment of the invention, the needle tip shielding device 100 comprises a body with a rear side 106, a front side 107, an outer surface 108 connecting the rear side 106 and the front side 107, a hole 102, preferably being circular, extending from the rear side 106 to the front side 107, and a resilient arm 103 extending from the front side 107 of the body. The rear side 106 and the front side 107 may be essentially flat and may be essentially parallel to each other. The hole 102 may extend essentially perpendicular to the plane of the rear side 106, and to the plane of the front side 107. The hole 102 is preferably positioned essentially at the center of the rear side 106, and at the center of the front side 107. The straight imaginary line L2 is coinciding with a point P1 at the edge between the rear side 106 and the outer surface 108, and with a point P2 at the shortest possible distance from point P1 at the edge between the front side 107 and the outer surface 108. At any pair of points P1 and P2, the part of line L2 extending from P1 to P2 preferably essentially coincides with the outer surface 108. The straight imaginary line L1 extending longitudinally through the center of the hole 102 is preferably essentially coinciding with the plane of any line L2. Any imaginary straight line, which is parallel with L1 and extending longitudinally through the hole 102, coincides with a point at the surface in between the attachment point 105 (not shown in FIG. 5) and the corner 104 of the resilient arm 103, when the resilient arm is in its resting state. The attachment point 105 is the edge which defines the transition between the front side 107 and the side of the resilient arm 103 which is closest to the hole 102. The corner 104 defines a sudden bend of the resilient arm 103 towards the plane of the front side 107, when the resilient arm 103 is in its resting state. Thus, the resilient arm 103 attains an L-shaped form, where the horizontal line of the L corresponds to a back-hooking elongation 110 of the resilient arm 103. The shape of the needle tip shielding device 100 according to the present invention has, in comparison to corresponding devices of the prior art, the advantage that it will act as a shield at the moment it disconnects from the catheter hub 200. Thereby it provides excellent protection per se against drops of blood or body fluid that may move outwards from the interior of the catheter hub 200 as the hollow needle 303 is removed.

Preferably, the resilient arm 103 is dimensioned, and attached at a position on the front side 107, such that it or the back-hooking elongation 110 may never contact the inner surface of the catheter hub 200 independent of the position of the hollow needle 303. Such a contact would potentially adventure the intended placement of the needle tip shielding device inside the catheter hub 200.

Preferably, the area of the back-hooking elongation 110 is fully covering the projecting area of the hole 102 when the needle tip 304 is clamped in the corner 104, i.e. protected, while the resilient arm 103 is maximally forced out of its resting state (as dependant on the rotation of the hollow needle 303 whereby the needle tip 304 attains different coordinates). This minimizes the risk of uncovering the needle tip 304 on the event that the resilient arm 103 gets bent by e.g. a sideways applied external force. Such a setup is not possible when more that one arm or jaw, corresponding to the resilient arm 103, is used in collaboration as they counteract each other in this regard.

According to one embodiment, the needle tip shielding device 100 has a circular shape, such that the rear side 106 and the front side 107 projects a circle from a view along the direction of the hollow needle 303.

According to one embodiment, the needle tip shielding device 100 has an elliptic shape, such that the rear side 106 and the front side 107 projects an ellipse from a view along the direction of the hollow needle 303.

According to one embodiment, the hole 102 is centered in the rear side 106 and in the front side 107.

According to one embodiment, the rear side 106 has a diameter in the range of 3 to 6 mm, preferably 3.9 to 4.3 mm, and even more preferred 4.1 to 4.15 mm.

According to one embodiment, the rear side 106 is provided with a cone-shaped elevation 109 through which the hole 102 is extending. The effective length of the hole 102 is thereby increased which, for example, allows a better guidance of the hollow needle 303 without having to increase the area of the outer surface 108 by increasing the distance between P1 and P2. Furthermore, the cone-shaped area might be provided with means known in the art, such as a circular scraper, which cleans off residues of e.g. blood from the hollow needle 303 as this is withdrawn.

According to one embodiment, the inner diameter of the hole 102 may be equal to or slightly larger than the outer diameter of the shaft of the hollow needle 303 to provide a sliding and directing engagement between the shaft and the needle tip shielding device 100. The inner surface of the hole 102 serves as a needle shaft contact area, in contrast to a needle shaft contact line in the metal clips according to known art, for contact with the outer surface of the shaft of the hollow needle 303, i.e. a sliding and directing engagement. This contact area may be maintained, while minimizing product material, i.e. product volume, by arranging the contact area fully or partly on the inside of the cone shaped elevation 109. The needle shaft contact area does not necessarily have to be a contact surface in the entire contact area, as long as the contact area substantially prevents a needle shaft positioned through the needle tip shielding device from swaying/wobbling in such way that the needle tip departs from the central axis of the hole 102. Preferably, the contact area is arranged such that a maximal contact with needle shaft is achieved without preventing the sliding of the hollow needle 303 through the needle tip shielding device 100. The needle shaft contact area may be an area of the needle tip shielding device 100 that surrounds and contacts the needle shaft, i.e. a hole 102 through which the hollow needle 303 runs. The inside surface of the hole 102, i.e. the needle shaft contact area, may be smooth, rough or provided with suitable shapes that contact the needle shaft. In general, the prevention of swaying/wobbling of the hollow needle 303 is better the longer the needle shaft contact area extends in the direction of the hollow needle 303. The extension of the needle shaft contact area, i.e. the longitudinal extension of the hole 102, is preferably as long as possible without adventuring any other intended functions of the needle tip shielding device. For example, the needle shaft contact area may preferably not be extended to such a degree that a simultaneous increase in the contact area with the inside of the catheter hub 200 results in that the needle tip shielding device 100 becomes unacceptable difficult to withdraw from the same. In this case, it is instead preferred to increase the extension of the cone shaped elevation 109. The cone shaped elevation 109 may, when positioned on the front side, not be extended to such a degree that the intended function of the resilient arm 103 is adventured. The extension of the needle shaft contact area may, for example, be 1 mm to 10 mm. Preferably, the relationship between the outer diameter of the shaft of the hollow needle 303 and the inner diameter of the hole 102 is such that the hollow needle 303 may easily slide therein when it is withdrawn or pushed forward, yet with a minimal difference between these diameters so that there is a minimal gap. Such a minimal difference, i.e. gap, will provide an adequate and optimal guidance of the hollow needle 303, and thus prevent undesired movement of the hollow needle 303 and the needle tip 304 in a direction perpendicular to the longitudinal direction of the hole 102 as the hollow needle 303 is pushed forwards or withdrawn.

Figure 7:
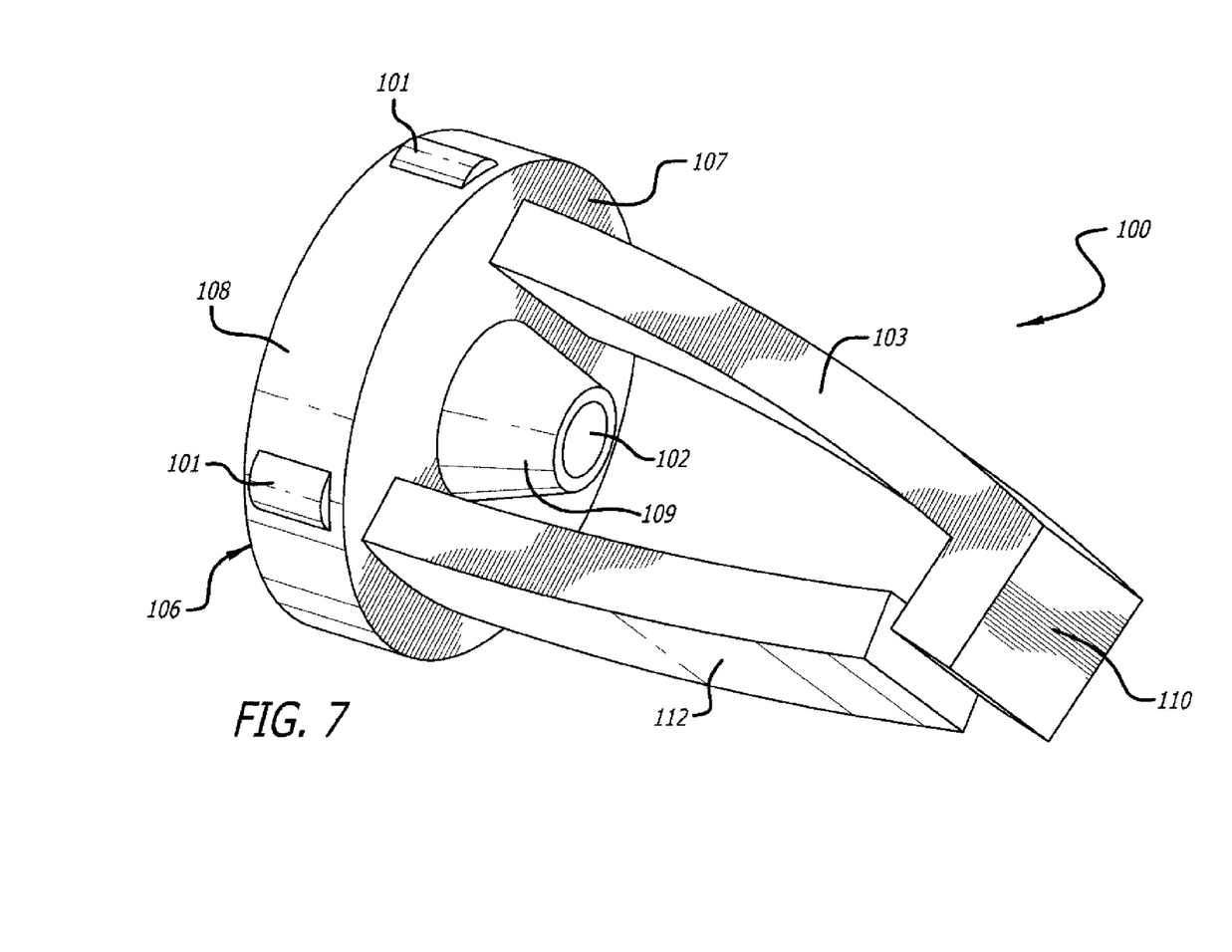
FIG. 7 is a perspective view of one embodiment of a needle tip shielding device comprising a front side provided with a cone shaped elevation, an outer surface provided with four (two of these not visible in the figure) evenly spread protuberances and a longitudinal arm extending from the front side, according to an embodiment of the invention.

According to one embodiment, the front side 107 may be provided with the cone-shaped elevation 109 (FIG. 7). The cone shaped elevation 109 then extends forward towards the needle tip, when the needle tip shielding device is arranged on a needle shaft. It is also possible to arrange the cone shaped elevation on the rear side 106, such as disclosed in FIG. 1. The arrangement, e.g. positioning and dimensions, of the resilient arm 103 and the cone shaped elevation is such that the intended function of the resilient arm 103 is not adventured. Thus, the resting position of the resilient arm 103 may be such that the needle tip 304 will always project, in the longitudinal direction of the hollow needle 303 positioned in the hole 102, onto a point of the surface of the resilient arm 103 which is positioned between a corner 104 and the attachment point 105 of the resilient arm 103 independent of the degree of rotation of the hollow needle 303 around its longitudinal axis. When the cone-shaped elevation 109 is positioned on the front side 107, the rear side 106 is preferably essentially flat. This allows for facile assembly of the needle tip shielding device 100 in the catheter hub 200 by pressing it into the same by employment of a tool which is contact with essentially the entire surface of the rear side 106.

According to one embodiment, the needle tip shielding device 100 is provided with the aforementioned protuberance 101 located on the outer surface 108. The protuberance 101 will make an imprint in the surrounding material of the catheter hub 200 when the needle tip shielding device 100 is positioned therein. The mechanical interaction between the protuberance 101 and the catheter hub 200, and the corresponding imprint caused by the former, will reduce the risks of unintentional disconnection of the needle tip shielding device 100 from the catheter hub 200.

According to one embodiment, the protuberance 101 is an annular protuberance extending in a continuous loop around the outer surface 108.

According to one embodiment, the protuberance 101 is an annular protuberance extending in a continuous loop around the outer surface 108, and being located in a plane perpendicular to L1.

According to another embodiment, the protuberance 101 may be a singularity or a plurality of protuberances independently selected from the group consisting of dots, straight elongated shapes, curved elongated shapes, V-shapes, and any other shape known in the art to make an imprint in an object in order to prevent relative movement versus this, such as the shapes on the surface of a tire optimized for use on soft ground.

According to one embodiment, the protuberance 101 may be made of a material with a hardness which is greater that the hardness of the inner surface of the catheter hub 200, in order to effectively accomplish an imprint in the latter. Preferably, the protuberance 101 is made of the same material as the rest of the needle tip shielding device 100, in order to allow for a facile and economically advantageous production of the same.

According to one embodiment, the type, multiplicity and dimension of protuberance 101 is selected such that no unintentional disconnection of the needle tip shielding device 100 from the catheter hub 200 may occur, yet allowing facile intentional disconnection when the hollow needle 303 is withdrawn. For example, the protuberance 101 may be an annular protuberance extending in a continuous loop around the outer surface 108 with a height in the range of 0.05 to 0.3 mm from the same.

According to one embodiment, the protuberance 101 may be a plurality of protuberances on the outer surface 108 (FIG. 7). These may begin at, or close to, the coiner between the rear side 106 and the outer surface 108 and extend in a plane essentially perpendicular to the plane of the rear side 106 and/or the front side 107, toward the front side 107. Preferably, they are evenly spread along the extension of the outer surface 108. Their extension along the outer surface 108 may be 10 to 95% of the distance between the rear side 106 and the front side 107 along the outer surface 108. Preferably, the endings being closest to the front side 107 consists of a smooth slope to allow facile insertion in a catheter hub 200. The plurality of protuberances on the outer surface 108 may have a height in the range of 0.01 to 0.3 mm, preferably 0.03 to 0.1 mm, and more preferred 0.04 to 0.06 mm, from the same. The plurality of protuberances on the outer surface 108 may consist of 1 to 20 individual protuberances, preferably 2 to 12, which may be of the same or of different lengths and/or heights. Preferably, they are of equal length and height.

According to one embodiment, the inclination of the outer surface 108 of the needle tip shielding device 100, i.e. the angle between lines L1 and L2, is within in the range from 0° to 10°, preferably in the range from 4° to 8°, and even more preferred 6°. Preferably, the inclination of the outer surface 108 is essentially the same as the inclination of the catheter hub 200 where the needle tip shielding device 100 is mounted when the catheter instrument 1000 is in the ready mode. This maximizes the contact surface between the outer surface 108 and the inside of the catheter hub 200, whereby accidental detachment of the needle tip shielding device 100 from the catheter hub 200 is hindered.

According to one embodiment, the inclination of the outer surface 108 of the needle tip shielding device 100, i.e. the angle between lines L1 and L2, is the same as the angle used in well known or standardized detachable conical fittings, such as fittings used for syringes, e.g. the Luer taper.

According to one embodiment, the needle tip shielding device 100 is made of a plastic material. Preferably, the plastic material has a suitable combination, for its intended purpose, of tenacity, rigidity, fatigue resistance, elasticity, and creep deformation resistance. The selection of a suitable plastic material may easily be made by the one skilled in the art. The one skilled in the art may also perform standard experiments in order to screen a range of plastic materials, whereby a suitable plastic material may be selected on the basis of the results of such experiments. A suitable plastic material has a high creep deformation resistance, i.e. it has a low tendency to slowly move or deform permanently under the influence of an applied external pressure. Hence, a catheter instrument, such as the catheter instrument 1000 of the present invention, comprising a needle tip shielding device 100 with protuberance 101, may be stored in the assembled ready mode for a prolonged time without extensive creep deformation of protuberance 101, which would otherwise make the needle tip shielding device 100 more prone to involuntary disconnection from the catheter hub 200. A suitable plastic material has, furthermore, a suitable elasticity and high three-dimensional memory to allow for the resilient arm 103 to retain its resting state and clamp the needle tip 304 even after prolonged storage, during which the resilient arm 103 has been forced out of this state. In addition, the tenacity of the plastic material is preferably such that the needle tip 304 may penetrate slightly into, but not through the same. The needle tip shielding device 100 may be made of a molded plastic material. Due to the specific configuration of the different parts of the needle tip shielding device 100 according to the embodiments of the present invention, the needle tip shielding device 100 may be molded, such as injection molded, into one homogenous piece and/or one integral unit, without interfaces in between the different parts thereof. Thus, advantageously, after production by any suitable molding procedure as known in the art, such as injection molding, all necessary parts of the needle tip shielding device 100 of the invention are already integrated without the need for costly and time consuming assembly of different separate parts.

An advantage of the use of a plastic material for the construction of the needle tip shielding device 100, in comparison to e.g. metal, is the greater freedom of variation of various details of the same. For example, a plastic needle tip shielding device 100 according to the invention may be more conveniently molded than the corresponding metallic article. Another advantage includes the possibility to colour-code a plastic needle tip shielding device 100 according to the invention, for example according to the needle size. Yet another advantage of a plastic needle tip shielding device 100 according to the invention is the fact that the needle tip 304 may penetrate slightly into the corner 104 of the resilient arm 103. This represents an "active" and safer shielding principle, in comparison to "passive" shielding of the prior art, whereby the resilient arm 103 is even further locked onto the needle tip 304 and hence additionally restricted from movement out of the safe position. Yet another advantage of a plastic needle tip shielding device 100 according to the invention is the fact that a metallic needle sliding through the hole 102, and on the resilient arm 103, does not give rise to a scraping vibration and sound of the uncomfortable type related to a metal needle sliding on and/or through a metal clip. Yet another advantage of a plastic needle tip shielding, device 100 according to the invention is the higher chemical inertness and/or resistance, in comparison to metal, towards e.g. corrosion and reaction with chemicals that might leak from the plastic surrounding constituted by a catheter hub and comprising silicon gaskets and the like. Yet another advantage of a needle tip shielding device 100, like a plastic needle tip shielding device 100, according to the invention, is that it may be molded and produced in one functional piece, i.e. it does not have to be assembled by the combination of more than one separate article like other corresponding devices of the prior art. Hence, a reduction in the cost of production is resulting. Yet another advantage of a plastic needle tip shielding device 100 according to the invention is the highly reduced tendency, in comparison to metal, of release of e.g. microscopic plastic chips by the scraping of the plastic catheter hub when the needle tip shielding device 100, or a corresponding device, is ejected from the former upon withdrawal of the needle. Accordingly, the tendency for formation of scrape marks, which may result in leakage through the affected connector, is greatly reduced.

According to one embodiment, the needle tip shielding device 100 is made of a thermoplastic polymer comprising crystalline and amorphous alternating regions.

According to one embodiment, the needle tip shielding device 100 is made of a plastic material selected from the group consisting of POM, PBTP, LCP, PA, PSU, PEI, PC, and PPO/SB.

According to one embodiment, the needle tip shielding device 100 is made of a thermoplastic elastomer selected from the group consisting of a styrenic block copolymer, a polyolefinic mixture, an elastomeric alloy, a thermoplastic polyurethane, a thermoplastic copolyester, and a thermoplastic polyamide.

According to one embodiment, the needle tip shielding device 100 is made of a plastic material selected from the group consisting of Styroflex®, Kraton®, Pellethane®, Pebax®, Amitel®, Hytrel®, Dryflex®, Santoprene®, Geolast®, Sarlink®, Forprene®, Alcryn®, and Evoprene®.

According to one embodiment, the needle tip shielding device 100 is made of a plastic material selected from the group consisting of medical grade liquid crystal polymer, for example Vectra® LCP, polyethylene, and ultra high molecular weight polyethylene.

According to one embodiment, the needle tip shielding device 100 is made of polysulfon or polyoxymetylen.

According to one embodiment, the angle inside the corner 104 is within the range from 60° to 110°, preferably 80° to 100°, more preferred 85° to 95°, and most preferred 90°.

According to one embodiment, the length of the back-hooking elongation 110, measured in its elongation from the corner 104 to the most protruding part, is at least 0.5 times the diameter of the hole 102, such as 0.5 to 6 times the diameter of the hole 102. It is preferably dimensioned such that no part of the resilient arm 103 is brought in contact with the inner surface of the catheter hub 200 at any location of the hollow needle 303 when the needle tip shielding device 100 is mounted in the catheter hut 200.

According to one embodiment, the back-hooking elongation 110 may comprise a groove with a partial circular shape, as well known in the art, provided and dimensioned to guide and allow the hollow needle 303 to slide thereon when withdrawn.

According to one embodiment, the resilient arm 103 may be dimensioned such that its most protruding part when being forced out of its resting position by the hollow needle 303 is in the range of 0.3 to 3 times the diameter of the front side 107, as measured from the attachment point 105.

According to one embodiment, the width and placement of the resilient arm 103 is such that no part of the resilient arm 103, or the back-hooking elongation 110, is brought in contact with the inner surface of the catheter hub 200 at any location of the hollow needle 303.

According to one embodiment, the width of the resilient arm 103 is in the range of 0.2 to 0.9 times the diameter of the front side 107 and selected such that it can not be bent aside to expose the needle tip 304 under normal circumstances.

According to one embodiment, the thickness and the material of the resilient arm 103 are selected such that the hollow needle 303 may never penetrate through the resilient arm 103 by a user under normal circumstances.

Figure 6:
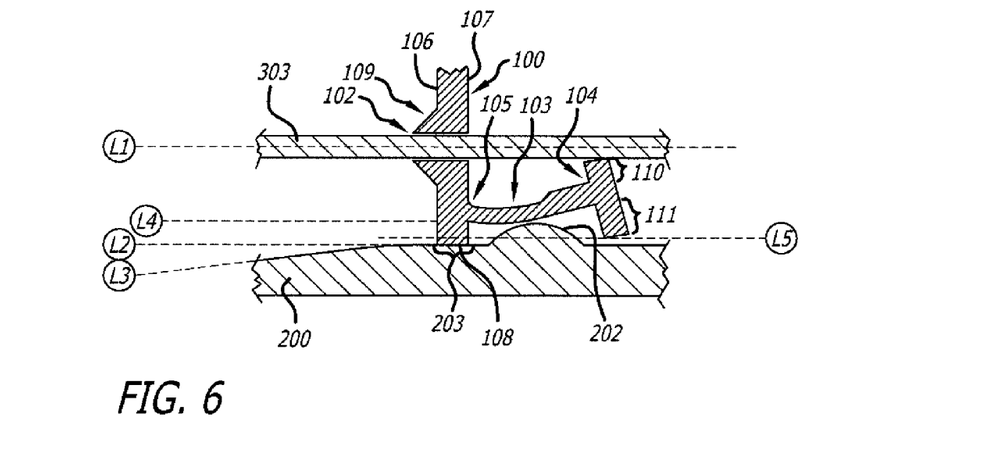
FIG. 6 is a partial cross section view from the side of a needle tip shielding device according to one embodiment, mounted in a catheter hub at a region where the tilt angle is practically 0° and wherein a resilient arm is provided with a back-dragging preventing elongation and wherein a catheter hub is provided with a catheter hub bump, according to an embodiment of the present invention.

With reference to FIG. 6, according one embodiment, the resilient arm 103 may be provided with a back-dragging preventing elongation 111, extending in a direction being within an angle of 0° to 45° opposite the direction of the back-hooking elongation 110. Preferably, the needle tip shielding device 100, when provided with the back-dragging preventing elongation 111, is mounted in the catheter hub 200 at a region 203 where the tilt angle is practically 0°, i.e. the angle between the line L1 and the line L2, in combination with the same inclination of the outer surface 108. The outer surface 108 may be provided with a protuberance 101, but this is not necessary at a low tilt angle, such as 0°. At such a low tilt angle, such as 0°, the needle tip shielding device may be held in place in the catheter hub 200 entirely by the friction between the outer surface 108 and the inner surface of the catheter hub 200. Furthermore, the material, of which the needle tip shielding device 100 is constructed, may be selected from a greater variety of materials since an imprint in the catheter hub 200 does not have to be made, as compared to the case with the existence of a protuberance 101. Preferably, the tilt angle of the catheter hub 200 is greater than 0°, such as 6°, in the region immediately behind, i.e. corresponding to the angle between L1 and L3 and being in the direction towards the rear end of the hollow needle 303, respectively, in order for the needle tip shielding device 100 to be easily removed from the catheter hub 200 when desired. The catheter hub 200 is provided with an annular catheter hub bump 202, extending around the inner surface of the catheter hub 200 in between the placement of the needle tip shielding device 100 and the back-dragging preventing elongation 111. When the hollow needle 303 is positioned in a forward direction, the back-dragging preventing elongation 111 is forced into a position so that the most extended part of the same is coinciding with point on an imaginary line L5, which is parallel with L1. L5 is coinciding with a point located on the catheter hub bump 202. In this state, the needle tip shielding device 100 is prevented from backwards unintentional movement as the back-dragging preventing elongation 111 would engage with, and get stuck on, the catheter hub bump 202. When the needle tip 304 has been withdrawn to the point where it is clamped by the back-hooking elongation 110 and/or the resilient arm 103, L5 is not coinciding with any point located on the catheter hub bump 202, hence, the needle tip shielding device 100 may be removed from the catheter hub 200. The back-dragging preventing elongation 111 and the catheter hub bump 202 have the function of a safety system which prevents the needle tip shielding device 100 from coming out of the catheter hub 200 in the case of an unintentional disconnection of the former from the inner wall of the latter.

With reference to FIG. 7, according to one embodiment, the front side 107 may be provided with a longitudinal arm 112 for additional protective shielding of the needle tip 304 or the hollow needle 303. Advantages of the longitudinal arm 112 include, for example, additional reduction of the risk for unintentional contact with e.g. the shaft of the hollow needle 303, which may be contaminated with e.g. blood, after disconnection of the needle tip shielding device 100 from the catheter hub 200. The longitudinal arm 112 is preferably arranged on the front side 107 such that it faces the resilient arm 103. The longitudinal arm 112 may be shaped, as known in the art, such that it maximizes the shielding of the exposed area of the needle shaft of the hollow needle 303 in front of the front side 107. It may, for example, be box-shaped with the broader side facing the hollow needle 303. The longitudinal arm 112 may be static or resilient. It is preferably resilient in order to allow facile production of the needle tip shielding device 100 in one piece by e.g. molding. The longitudinal arm 112 is preferably never contacting the resilient arm 103 in order to not adventure the intended function of the latter, i.e. its needle tip protective function. The longitudinal arm 112 may or may not contact the inside of the catheter hub 200 or the needle shaft of the hollow needle 303. It may, however, preferably never contact either of these.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A plastic needle tip shielding device comprising:
   a body with a rear side, a front side, an outer surface connecting said rear side and said front side, and a hole extending from said rear side to said front side, said outer surface having an outer diameter configured to engage an inner surface of a catheter hub;
   a resilient arm connected to and extending from an attachment point on said front side of said body and with said front side spanning said outer diameter of said outer surface, said attachment point being located between said outer surface and said hole;
   at least one protuberance on said outer surface; and
   an elevation about said hole;
   wherein said resilient arm has a resting state, from which it may be forced to yield free passage through said hole in an axial direction of said body, said resilient arm being adapted for clamping a needle tip of a hollow needle extending through said hole in a direction from said rear side to said front side, when said resilient arm is in said resting state;
   wherein any straight imaginary line extending longitudinally through said hole in the axial direction of said body coincides with said resilient arm, when said resilient arm is in said resting state; and
   wherein said plastic needle tip shielding device includes a thermoplastic polymer.

2. The needle tip shielding device according to claim 1, wherein said plastic needle tip shielding device is made of a thermoplastic polymer comprising crystalline and amorphous alternating regions.

3. The needle tip shielding device according to claim 1, wherein said plastic needle tip shielding device is made of a plastic material selected from the group consisting of POM, PBTP, LCP, PA, PSU, PEI, PC, and PPO/SB.

4. The needle tip shielding device according to claim 1, wherein said plastic needle tip shielding device is made of a thermoplastic elastomer selected from the group consisting of a styrenic block copolymer, a polyolefin mixture, an elastomeric alloy, a thermoplastic polyurethane, a thermoplastic copolyester, and a thermoplastic polyamide.

5. The needle tip shielding device according to claim 1, wherein said resilient arm comprises a corner and a back-hooking elongation, said resilient arm together with said back-hooking elongation thereof having an L-shaped form.

6. The needle tip shielding device according to claim 1, the at least one protuberance including an annular protuberance.

7. The needle tip shielding device according to claim 5, wherein the length of said back-hooking elongation, measured from said corner to a most protruding part, is 0.5 to 6 times the diameter of said hole.

8. The needle tip shielding device according to claim 1, wherein said resilient arm includes a corner, and an angle defined by said corner is within the range from 60° to 110°.

9. The needle tip shielding device according to claim 1, wherein said front side further comprises a longitudinal arm extending from said front side for additional protective shielding of said needle tip of said hollow needle.

10. A catheter instrument comprising:
  a catheter hub;
  a needle unit;
  a needle tip shielding device including a body with a rear side, a front side, an outer surface connecting said rear side and said front side, a hole extending from said rear side to said front side, and a resilient arm located between said outer surface and said hole, said outer surface having an outer diameter configured to engage an inner surface of a catheter hub, said resilient arm being connected to and extending from an attachment point on said front side of said body and with said front side spanning said outer diameter of said outer surface;
  at least one protuberance on said outer surface; and
  an elevation about said hole;
  wherein said needle unit is provided with connecting means for connection to said catheter hub, with connecting means for connection to an external device, and is fixed around a rear end of a hollow needle; and
  wherein said catheter hub is connected to a catheter extending longitudinally in the same direction as said hollow needle when said needle unit is connected by said connecting means to said catheter hub.

11. The needle tip shielding device according to claim 1, the elevation extending from said rear side.

12. The catheter instrument according to claim 10, the elevation extending from said rear side.

13. The needle tip shielding device according to claim 5, further comprising a second elongation extending in an opposite direction of said back-hooking elongation.

14. The needle tip shielding device according to claim 1, the at least one protuberance being configured to contact said inner surface of said catheter hub.

15. The catheter instrument according to claim 10, the at least one protuberance being configured to contact said inner surface of said catheter hub.

16. The needle tip shielding device according to claim 1, the at least one protuberance extending in a loop around said outer surface.

17. The needle tip shielding device according to claim 1, the at least one protuberance being located in a plane perpendicular to an axis extending longitudinally through said hole.

18. A shielding device comprising:
  a body with a rear side, a front side, an outer surface connecting said rear side and said front side, and a hole extending from said rear side to said front side, said outer surface having an outer diameter configured to engage an inner surface of a catheter hub;
  a resilient arm connected to and extending from an attachment point on said front side of said body and with said front side spanning said outer diameter of said outer surface, said attachment point being located between said outer surface and said hole;
  at least one protuberance on said outer surface; and
  an elevation about said hole.

19. The shielding device according to claim 18, the elevation extending from said rear side.

20. The shielding device according to claim 18, the at least one protuberance being configured to contact said inner surface of said catheter hub.

* * * * *